United States Patent [19]

Fields

[11] 4,287,349

[45] Sep. 1, 1981

[54] BETA-ALKYL (OR ARYL) BETA-HYDROXYETHYL HETEROCYCLIC SULFOXIDES

[75] Inventor: Ellis K. Fields, River Forest, Ill.

[73] Assignee: Standard Oil Company (Indiana), Chicago, Ill.

[21] Appl. No.: 32,269

[22] Filed: Apr. 23, 1979

[51] Int. Cl.³ .................... C07D 277/64; C07G 13/00
[52] U.S. Cl. ................................. 548/166; 204/158 R
[58] Field of Search .................. 260/306; 204/158 R; 548/166

[56] References Cited

U.S. PATENT DOCUMENTS

| | | | |
|---|---|---|---|
| 2,280,792 | 4/1942 | Bruson | 260/306 |
| 2,777,852 | 1/1957 | Steiger | 548/166 |
| 2,777,853 | 1/1957 | Steiger | 548/166 |
| 3,247,258 | 4/1966 | Anderson | 204/158 R |
| 3,849,431 | 11/1974 | Gallay et al. | 260/306 |
| 3,985,762 | 10/1976 | Dransch et al. | 260/306 |
| 4,040,921 | 8/1977 | Fields | 204/158 R |

*Primary Examiner*—Donald G. Daus
*Assistant Examiner*—D. B. Springer
*Attorney, Agent, or Firm*—William C. Clarke; William T. McClain; William H. Magidson

[57] ABSTRACT

Beta-alkyl (or aryl) beta-hydroxyethyl heterocyclic sulfoxides are prepared by reacting an olefin and 2-mercaptobenzothiazole with oxygen in the presence of a dye sensitizer using visible light as an energy source at a temperature from $-10°$ to $70°$ C.

5 Claims, No Drawings

BETA-ALKYL (OR ARYL) BETA-HYDROXYETHYL HETEROCYCLIC SULFOXIDES

BACKGROUND OF THE INVENTION

This invention relates to beta-alkyl (or aryl) beta-hydroxyethyl heterocyclic sulfoxides prepared by reacting an olefin, 2-mercaptobenzothiazole and oxygen in the presence of a dye sensitizer using visible light as an energy source.

DESCRIPTION OF THE PRIOR ART

Beta-hydroxyalkylsulfoxides have been found to be useful as detergents, insect repellants, anti-static agents and petroleum additives. Anderson, U.S. Pat. No. 3,247,258 which is incorporated by reference, discloses that in order to obtain beta-hydroxyalkylsulfoxides in good yields, the mercaptan (or thiol), the olefin and the oxygen must be contacted above 80° C. as substantially no reaction occurs below that temperature. Another critical feature according to Anderson is the method of carrying out the reaction. With certain olefins and mercaptans such as indene, styrene and thiophenol, the reaction occurs first by mixing the olefin and the mercaptan with the oxygen being bubbled thereafter through the mixture. Other patents such as Oswald et al, U.S. Pat. No. 3,043,824 and Goodhue et al, U.S. Pat. No. 3,210,243, which are each incorporated by reference, disclose preparing beta-hydroxyalkylsulfoxides through (1) a co-oxidation route using a hydroperoxide or through (2) oxidation of the sulfide by means of hydrogen peroxide. Oswald indicates that the preparation of hydroperoxide products by olefin-mercaptan co-oxidation to the sulfoxide requires chain initiators, e.g., ultraviolet light or the addition of peroxide compounds (hydroperoxides). Such initiators, indicates Oswald, are especially important when aliphatic mercaptans or n-olefins are co-oxidized. In the absence of such catalysts, some co-oxidation reactions have extremely long induction periods and are not practical to carry out. Oswald indicates the olefin-mercaptan co-oxidation temperature may range from $-50°$ C. to $0°$ C., although Oswald does report two attempts to co-oxidize to the hydroperoxide at 20° C. (Example 2) with a reaction time of 16 hours. Goodhue teaches that the preparation of the sulfoxide using hydrogen peroxide is a three-step synthesis through the sulfide which in turn is prepared from the mercaptan with epichlorohydrin. Fields, U.S. Pat. No. 4,040,921, teaches a process for beta-hydroxyalkylsulfoxides by reacting an olefin and a thiol with oxygen in the presence of a dye sensitizer using visible light at a temperature from $-10°$ to 70° C.

However in the prior art as it pertains to beta-hydroxyalkylsulfoxides, there has been no teaching that beta-alkyl (or aryl) beta-hydroxyethyl heterocyclic sulfoxides have been prepared from 2-mercaptobenzothiazole and olefinically unsaturated compounds in the presence of oxygen, using actinic radiation as an energy source preferably in the presence of a dye sensitizer.

The general object of this invention accordingly is to produce as new compounds beta-alkyl (or aryl) beta-hydroxyethyl heterocyclic sulfoxides by a process directly from 2-mercaptobenzothiazole in good yield at ambient temperatures by co-oxidation with an olefin using oxygen to obtain an increased rate of reaction and short reaction time with consequent economic industrial advantage. Other objects appear hereinafter.

SUMMARY OF THE INVENTION

This invention relates to beta-alkyl (or aryl) beta-hydroxyethyl heterocyclic sulfoxides and to a process for their preparation by reacting an olefin, 2-mercaptobenzothiazole and oxygen in the presence of a dye sensitizer using visible light as an energy source at a temperature from about $-10°$ to 70° C., preferably $+10°$ to 20° C.

DETAILED DESCRIPTION OF THE INVENTION

Beta-alkyl (or aryl) beta-hydroxyethyl heterocyclic sulfoxides, so named for convenience but also named 1-(2-hydroxyalkyl) 2-benzothiazolyl sulfoxides and 1-(2-hydroxyaralkyl) 2-benzothiazolyl sulfoxides, are prepared by an improved process by reacting an olefin, 2-mercaptobenzothiazole and oxygen in the presence of a dye sensitizer using visible light as an energy source. The general equation of the reaction is

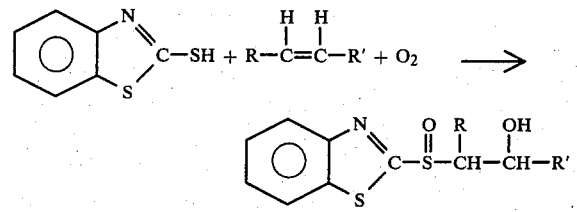

wherein R and R' can be identical or different groups, such as alkyl, aryl, aralkyl, alkaryl and heterocyclic groups that can contain substituents such as alkoxy, carboxy, nitro, halo and alkylthio groups. R can be and is preferably hydrogen and, in the case of ethylene, both R and R' are hydrogen. The beta-alkyl (or aryl) beta-hydroxyethyl heterocyclic sulfoxide compounds are active against microorganisms and have surfactant properties. These compounds can be used in solvents, emulsions and powdered solids in concentrations of 0.001 (wt) % to 10 (wt) %.

For the purpose of this invention it is essential that a dye sensitizer be used. If visible light is employed without the use of the dye sensitizer, yields of beta-alkyl (or aryl) beta-hydroxyethyl heterocyclic sulfoxides are substantially lower. An expected low yield or even lack of reaction is consistent with Oswald, U.S. Pat. No. 3,043,824, in Examples III and IV wherein control solutions unexposed to ultraviolet light, but presumably to visible light, resulted in either little or no co-oxidation products.

In general, the process for preparing beta-alkyl (or aryl) beta-hydroxyethyl heterocyclic sulfoxides requires the reacting of an olefinically unsaturated compound containing 2 to 30 carbon atoms with a 2-mercaptobenzothiazole in the presence of oxygen. These olefinically unsaturated compounds can be aliphatic, aromatic, cyclic and heterocyclic. These compounds are preferably terminal olefins and can be visualized as being of the formula RCH=CHR' where R' is preferably hydrogen. However, R and R' can be defined also as radicals and can be the same or different straight chain or branched chain alkyl groups containing 1 to 22 carbon atoms (such as methyl, ethyl, i-butyl, octyl, etc., to docosyl groups), preferably 4 to 18 carbon atoms; aralkyl groups as beta-phenethyl, alkylated aryl groups as tolyl or xylyl, heterocyclic alkyl groups as picolyl and thiazylmethyl, cycloalkyl groups as cyclopentylmethyl and cyclohexylmethyl, the last four containing 5 to 30 carbon atoms, preferably 6 to 24 carbon atoms, and the same groups containing substituents such as halogens (fluorine, chlorine, bromine and iodine), nitro, alkoxy (methoxy, ethoxy, propoxy, butoxy) or dialkylamino groups. R and R' can be joined and comprise a ring containing five to eight carbon atoms. Examples where R and R' are so joined to comprise a ring are cyclopentadiene and cyclooctatetraene. Examples of olefinically unsaturated aliphatic, aromatic and alicyclic compounds are ethylene, propylene, 1-butene, 1-pentene, 1-hexene, 1-octene, 1-decene, 1-dodecene, 1-octadecene, cyclohexene, cyclopentene, cyclooctene, cyclododecene, bicycloheptene, octahydronaphthalene, styrene, alpha-methylstyrene, 3-phenyl-1-propene, 1,1-diphenylethylene, 3,4-diphenylbutene-1, 4-vinyltoluene, 1- and 2-vinylnaphthalene, 4-vinylbiphenyl, 1-vinyl anthracene, 2- and 4-vinylpyridine, 3-vinylthiophene, 2-vinylfuran, 2- and 4-vinylquinoline, 1-vinylphenanthridene, 2-vinyl-1,3,5-triazene, m- and p-chlorostyrene, acrylic acid, allyl alcohol, diallyl terephthalate, undecylenyl alcohol, oleic acid, linoleic acid, dicyclopentadiene, norbornadiene, vinyl cyclohexene, and cyclo-dodecatriene.

Preferably the olefinically unsaturated compound comprises a hydrocarbon containing 2 to 16 carbon atoms such as ethylene, propylene, 1-butene, 1-pentene, 1-octene, 1-dodecene, 1-tetradecene, 1-hexadecene, and styrene. These are preferred because they are cheap and react readily, comprising easily available compounds for providing a range of derivative short-chain water-soluble compounds to long-chain oil-soluble compounds. For example, ethylene results in 1-(2-hydroxyethyl)2-benzothiazolyl sulfoxide, 1-octene results in 1-(2-hydroxyoctyl) 2-benzothiazolyl sulfoxide, 1-dodecene in 1-(2-hydroxydodecyl)2-benzothiazolyl sulfoxide, 1-butene in 1-(2-hydroxybutyl)2-benzothiazolyl sulfoxide, styrene in 1-(2-hydroxyphenylethyl) 2-benzothiazolyl sulfoxide.

The molar ratios of the reactants i.e., the 2-mercaptobenzothiazole, olefins, oxygen, that can be used, can vary considerably. The mercaptan-olefin ratio is between 0.001 to 5 moles of mercaptan per mole of olefin. In the practice of my invention substantially equimolar amounts of olefin and mercaptan are preferred. Use of a solvent such as heptane, hexane, benzene, acetone, or dioxane at concentrations of 1 to 85 weight percent is convenient. When water-miscible solvents such as acetone or dioxane are used, water up to 50% by weight or organic solvent may be incorporated. In such cases, or when water is used with immiscible solvents such as heptane or benzene up to 50% by weight, phase-transfer agents such as cetyl trimethyl ammonium chloride, benzyl triethyl ammonium chloride, benzyl triphenyl phosphonium chloride, etc., are incorporated at concentrations of 0.001 to 1% by weight of total solvent.

Heptane is the preferred solvent: 10 to 20 weight percent is the preferred concentration range of the reactants.

In the practice of my invention it is essential that at least one optically sensitizing dye be used in conjunction with the application of visible light. For purposes of my invention, the term dye sensitizer can be defined as being an organic dye which increases spectral response. Typical dye sensitizers are fluorescein derivatives, methylene blue, certain porphyrins and polycyclic aromatic hydrocarbons. For purposes of this invention, suitable dye sensitizers include Rose Bengal, methylene blue and Eosin.

Rose Bengal and methylene blue are the preferred dye sensitizers dissolved in acetone at 0.1–5% by weight. Sufficient dye is added to give final concentrations of 0.002 to 1% weight in the total reaction mixture; 0.05 to 0.25% by weight is preferred. Alternatively the dye may be introduced bound to an ion-exchange resin in a relatively insoluble form, e.g., anionic Rose Bengal or Eosin attached to the strongly basic anion exchange resin Amberlite IRA-400 (Rohm and Haas, Philadelphia Pa.) or cationic methylene blue attached to the strongly acidic cation exchange resin Amberlite IRC-200 (J. R. Williams et al., *Tetrahedron Letters* 4603 (1973)).

My reaction may be run in any type of open or sealed vessel, suitably agitated. A particularly useful apparatus for the reaction is Parr Pressure Reaction Apparatus, Item #3911, made by the Parr Instrument Company of Moline, Ill. This apparatus consists of a heavy-walled clear pyrex bottle connected with a tank of oxygen under pressure; the bottle is shaken vigorously during the reaction. Pressures of oxygen of 1 to 250 psig may be used; 15 to 50 psig $O_2$ are convenient pressures in the laboratory although, commercially, pressures over 100 psig are preferred. The bottle is illuminated with visible light such as ordinary incandescent or photoflood bulbs of 50–500 watts, preferably mounted in reflectors with the light source $1\frac{1}{2}$ to 3 inches from the vessel.

The lamps used were General Electric 500 watt photoflood or incandescent bulbs and a General Electric 275 watt Sunlamp. Specifications of the G.E. 500 watt photoflood lamp require 1.61 radiated watts from 280 to 400 nanometers, and 6.9 radiated watts from 400 to 700 nanometers, the range of visible light. The G.E. Sunlamp has 4.47 radiated watts in the ultraviolet range from 280 to 400 nanometers, and 7.03 radiated watts in the visible light range of 400 to 700 nanometers.

Since the radiated wattage of the Sunlamp is greater than that of the incandescent bulb in the visible light range, it is indeed surprising that yield improvement and shortened reaction time occurred with use of visible light plus a dye sensitizer over that obtained by use of an ultraviolet light source as taught by the prior art, i.e., U.S. Pat. No. 3,043,824.

Reaction is continued until the calculated amount of oxygen has been absorbed as shown by pressure drop; times of 1 to 100 hours may be used, depending on the nature of the olefin, the thiol, and the pressure of oxygen. Workup generally consists of evaporating the reaction mixture at 30°–60° C. and 0.1–1 Torr., conveniently in a rotating RINCO evaporator (BUCHI Vacuum Rotary Evaporator ROTAVAPOR EL, Rinco Instrument Company, Inc., Greenville, Ill.).

In order to facilitate a clear understanding of the invention, the process of preparing beta-alkyl (or aryl) beta-hydroxyethyl heterocyclic sulfoxides from the reaction product of an olefin and a mercaptan with the use of oxygen, the following specific embodiments are described in detail. It should be understood, however, that the detailed expositions of the application of this process, while indicating preferred embodiments, are given by way of illustration only since various changes and modifications within the spirit and scope of the invention will become apparent to those skilled in the art from this detailed description.

EXAMPLE I

A mixture of 16.7 g (0.1 mole) of 2-mercaptobenzothiazole, 150 ml of dioxane, 5 ml of 0.5% methylene blue in acetone, and 18 ml (0.1 mole) of 1-octene was shaken in a Parr shaker under 25 psig $O_2$ and irradiated with a 275 watt G.E. Sunlamp for 72 hours at 25° C. The mixture was filtered and evaporated in a Rinco rotary evaporator at 40° C. and 0.5–1 Torr. to give 30.1 g (96.8 mole %) of brown, viscous product 1-(2-hydroxyoctyl 2-benzothiazolyl sulfoxide. It analyzed C, 57.8%; H, 6.6%; N, 4.2%; S, 20.3%.

Calculated for $C_{15}H_{21}NS_2O_2$; C, 57.9%; H, 6.8%; N, 4.5%; S, 20.6%.

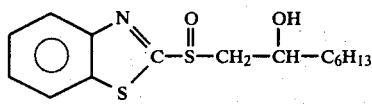

EXAMPLE II

The same mixture as in Example I except that 16.8 g (0.1 mole) of 1-dodecene instead of 1-octene, was treated in the identical fashion to give 34.53 g (96.7 mole %) of dark brown, viscous product 1-(2-hydroxydodecyl) 2-benzothiazolyl sulfoxide. It analyzed C, 60.9%; H, 7.8%; N, 3.8%; S, 17.4%.

Calculated for $C_{19}H_{29}NS_2O_2$; C, 61.1%; H, 8.1%; N, 3.9%; S, 17.9%.

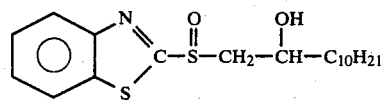

EXAMPLE III

The effectiveness of the novel compounds as surfactants in lowering interfacial tension between solvent-extracted 5 W oil and water was measured, using a Cenco-Du Nouy Interfacial Tensiometer #70545 with a 6 cm platinum-iridium ring at 25° C., with double-distilled water, with these results.

| Product of Example No. | Concentration, (wt) % | Interfacial Tension, Dynes/cm |
|---|---|---|
| Control | 0 | 34.13 |
| I | 0.37 | 13.93 |
| II | 0.4 | 9.41 |

EXAMPLE IV

The compounds of Examples I and II were tested as biocides and inhibitors for the growth of microorganisms by this test: 25 g of agar preparation were placed in standard Petri dishes. The agar preparation consisted of 23.5 g of Bacto Plate Count Agar, Difco Laboratories, Detroit, Mich., dissolved in 1 liter of water. Plate Count Agar contains a standard USP formula for nutrient agar, consisting of

| | |
|---|---|
| 5 g. | Pancreatic digest of casein |
| 2.5 g | Yeast extract |
| 1 g | Glucose |
| 15 g | Agar |

Four Petri dishes were untreated and used as controls. To the others, in duplicate, were added 2.5 ml of 1% acetone solutions of the products of Examples I and II. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results are shown in the table.

| Product, Example No. | Rating |
|---|---|
| I | 0,0 |
| II | 0,0 |
| Controls | 5,5,5,5 |

What is claimed is:
1. A beta-alkyl beta-hydroxyethyl 2-benzothiazolyl sulfoxide of the formula

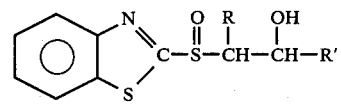

wherein R is hydrogen and R' is selected from the group consisting of alkyl groups of 1 to 22 carbon atoms, phenyl and hydrogen.

2. The compound of claim 1 which is 1-(2-hydroxyethyl) 2-benzothiazolyl sulfoxide.

3. The compound of claim 1 which is 1-(2-hydroxyoctyl) 2-benzothiazolyl sulfoxide.

4. The compound of claim 1 which is 1-(2-hydroxydodecyl) 2-benzothiazolyl sulfoxide.

5. The compound of claim 1 which is 1-(2-hydroxyphenylethyl) 2-benzothiazolyl sulfoxide.

* * * * *